(12) United States Patent
Silcock et al.

(10) Patent No.: US 8,058,499 B2
(45) Date of Patent: Nov. 15, 2011

(54) ABSORBENT WOUND DRESSING CONTAINING A HYDROGEL LAYER

(75) Inventors: Derek Silcock, North Yorkshire (GB); Andrew James Kirkwood, Hull (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 0 days.

(21) Appl. No.: 10/496,158

(22) PCT Filed: Nov. 22, 2002

(86) PCT No.: PCT/GB02/05253
§ 371 (c)(1),
(2), (4) Date: Nov. 4, 2004

(87) PCT Pub. No.: WO03/045294
PCT Pub. Date: Jun. 5, 2003

(65) Prior Publication Data
US 2005/0256437 A1    Nov. 17, 2005

(30) Foreign Application Priority Data
Nov. 23, 2001 (GB) .................... 0128152.6

(51) Int. Cl.
*A61F 13/00* (2006.01)
(52) U.S. Cl. .......... 602/48; 41/42; 41/46; 41/47
(58) Field of Classification Search .......... 602/41–59; 424/443–449; 604/358–402
See application file for complete search history.

(56) References Cited

U.S. PATENT DOCUMENTS

| | | | | |
|---|---|---|---|---|
| 3,428,043 A * | 2/1969 | Shepherd | ............ | 604/304 |
| 3,890,974 A * | 6/1975 | Kozak | ............ | 604/368 |
| 3,929,135 A * | 12/1975 | Thompson | ............ | 604/385.08 |
| 4,909,244 A * | 3/1990 | Quarfoot et al. | ............ | 602/48 |
| 5,010,883 A * | 4/1991 | Rawlings et al. | ............ | 602/52 |
| 5,160,328 A * | 11/1992 | Cartmell et al. | ............ | 604/307 |
| 5,328,450 A * | 7/1994 | Smith et al. | ............ | 602/59 |
| 5,447,492 A * | 9/1995 | Cartmell et al. | ............ | 602/58 |
| 5,501,661 A * | 3/1996 | Cartmell et al. | ............ | 602/58 |
| 5,635,201 A * | 6/1997 | Fabo | ............ | 424/443 |
| 5,643,187 A * | 7/1997 | Næstoft et al. | ............ | 602/43 |
| 6,468,383 B2 * | 10/2002 | Kundel | ............ | 156/272.2 |
| 6,566,575 B1 * | 5/2003 | Stickels et al. | ............ | 602/41 |
| 6,566,577 B1 * | 5/2003 | Addison et al. | ............ | 602/56 |

(Continued)

FOREIGN PATENT DOCUMENTS

EP    0 541 391 B1    6/1998

(Continued)

OTHER PUBLICATIONS

Registered Mark ESTANE 5714F, Registration No. 2533691, Registration Date Jan. 29, 2002, 6 pages.

(Continued)

*Primary Examiner* — Kim Lewis
(74) *Attorney, Agent, or Firm* — Morgan, Lewis & Bockius LLP

(57) ABSTRACT

A wound dressing comprising: a liquid-permeable top sheet having a wound facing surface and a back surface, said top sheet being adapted to block or restrict passage of liquid from the back surface to the wound facing surface; and an insoluble hydrogel layer adjacent to the back surface of the top sheet.

22 Claims, 2 Drawing Sheets

U.S. PATENT DOCUMENTS

| | | | |
|---|---|---|---|
| 6,600,085 B2 * | 7/2003 | Sun et al. | 602/56 |
| 6,861,067 B2 * | 3/2005 | McGhee et al. | 424/445 |
| 2003/0153860 A1 * | 8/2003 | Nielsen et al. | 602/43 |
| 2005/0251082 A1 * | 11/2005 | Del Bono | 602/41 |

FOREIGN PATENT DOCUMENTS

| | | |
|---|---|---|
| GB | 1 280 631 | 7/1972 |
| GB | 1 526 778 | 9/1978 |
| WO | WO 00/07638 A1 | 2/2000 |
| WO | WO 02/38097 A1 | 5/2002 |

OTHER PUBLICATIONS

Registered Mark VISPORE, Registration No. 1210473, Registration Date Sep. 28, 1982, 5 pages.

Registered Mark PLURONIC, Registration No. 0547988, Registration Date Sep. 11, 1951, 4 pages.

* cited by examiner

ABSORBENT WOUND DRESSING CONTAINING A HYDROGEL LAYER

CROSS-REFERENCE TO RELATED APPLICATIONS

This application is the national stage filing under 35 U.S.C. §371 of International Application No. PCT/GB02/05253 filed Nov. 22, 2002 and published Jun. 5, 2003, as International Publication No. WO 03/045294 which in turn claims priority under 35 U.S.C. §119 to Great Britain Patent Application No. 0128152.6, filed Nov. 23, 2001.

FIELD OF THE INVENTION

The present invention relates to wound dressings incorporating an absorbent structure and a hydrogel layer for the maintenance of a suitable moisture level at the surface of wounds.

DETAILED DESCRIPTION OF THE INVENTION

It is known that the maintenance of a moist wound environment promotes the healing of wounds, especially burns and chronic wounds such as ulcers. However, it is also desirable to avoid excessive moisture or pooling of wound exudate on the wound, since liquid exudate causes maceration of skin adjacent to the wound and other difficulties. Furthermore, liquid exudate can leak from the wound site and contaminate clothes or bedding.

In practice, it is difficult to maintain the desired moisture level at the wound site because the rate of wound fluid production varies from wound to wound, and over time for any single wound. This can necessitate frequent dressing changes and a range of dressing types to treat different wounds.

It is an object of the present invention to provide structures for use as or in improved multilayer dressings for the treatment of a wide range of wounds.

The present invention provides a wound dressing comprising: a liquid-permeable top sheet having a wound facing surface and a back surface, said top sheet being adapted to block or restrict passage of liquid from the back surface to the wound facing surface; and a hydrogel layer adjacent to the back surface of the top sheet.

Preferably, the dressing further comprises a backing layer over the back face of the top sheet. The backing layer supports the top sheet and an intermediate absorbent layer (where present) and preferably provides a barrier to passage of microorganisms through the dressing. The backing layer may extend beyond at least one edge of the absorbent layer to provide an adhesive-coated margin adjacent to the said edge for adhering the dressing to a surface, such as to the skin of a patient adjacent to the wound being treated. An adhesive-coated margin may extend around all sides of the absorbent layer, so that the dressing is a so-called island dressing. However, it is not necessary for there to be any adhesive-coated margin.

Preferably, the backing layer is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 g/m$^2$/24 hrs, preferably 500 to 2000 g/m$^2$24 hrs at 37.5 C at 100% to 10% relative humidity difference. The backing sheet thickness is preferably in the range of 10 to 1000 micrometers, more preferably 100 to 500 micrometers.

The MVTR of the dressing according to the present invention as a whole is lower than that of the backing sheet alone, because the top sheet partially obstructs moisture transfer through the dressing. Preferably, the MVTR of the dressing (measured across the island portion of the dressing) is from 20% to 80% of the MVTR of the backing sheet alone, more preferably from 20% to 60% thereof, and most preferably about 40% thereof. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 g/m$^2$, and more preferably 50 to 150 g/m$^2$. Polyurethane-based pressure sensitive adhesives are preferred.

Preferably, the adhesive layer extends outwardly from the absorbent layer and the top sheet to form an adhesive-coated margin on the backing sheet around the adhesive layer as in a conventional island dressing.

The area of the optional absorbent layer is typically in the range of from 1 cm$^2$ to 200 cm$^2$, more preferably from 4 cm$^2$ to 100 cm$^2$.

The optional absorbent layer may be any of the layers conventionally used for absorbing wound fluids, serum or blood in the wound healing art, including foams, sponges, gauzes, and nonwoven fabrics, and combinations thereof. Superabsorbents or hydrogels may be dispersed in the optional absorbent layer to improve liquid absorbency and retention. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 g/m$^2$, such as 100-400 g/m$^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25° C.

The optional absorbent layer is a separate layer from the hydrogel layer in the wound dressings according to the present invention, and is located on the opposite side of the hydrogel layer from the top sheet. In certain embodiments the hydrogel layer and the optional absorbent layer are adjacent, and in certain embodiments they are laminated together.

The optional absorbent layer may additionally comprise one or more active therapeutic or antimicrobial agents. Suitable therapeutic agents include growth factors, analgesics, local anaesthetics and steroids. Suitable antimicrobial agents include antiseptics such as silver compounds (e.g. silver sulfadiazine) and chlorhexidine, and antibiotics. The therapeutic or antimicrobial agents are usually added in an amount of from 0.01% to 5% by weight, based on the dry weight of the absorbent layer. Provision of the antimicrobial in the absorbent layer may be preferable for two reasons (1) Simple manufacturing route, and (2) Having the antimicrobial away from the wound would prevent unnecessary exposure to the antimicrobial when it may not be needed, e.g. drier wounds. In the presence of higher exudate, higher levels of the antimicrobial will be released as the absorbent layer becomes wet. Whilst the directional top sheet should restrict the flow of exudate back to the wound (to some extent through surface tension of the liquid), the antimicrobial should go against the concentration gradient and pass back through the perforated sheet and into the wound. It is know that antimicrobial components such as silver ions can be transported through relatively low levels of moisture.

The top sheet of the wound dressing according to the invention is liquid permeable, but acts to block or restrict the flow of liquid from the back surface to the wound site. That is to say, the top sheet allows fluid to pass through the top sheet from the wound site, but blocks or restricts flow of the fluid back through the top sheet onto the wound (also known as wet-back). Such non-wetting top sheets may for example be made from porous non-woven fabrics comprising a layer of hydrophobic fibers, or having a hydrophobic finish applied to at least the outer surface thereof. Preferably, the top sheet has greater liquid permeability to the flow of liquid away from the wound facing surface than to the flow of liquid towards the wound facing surface.

The top sheet film may be formed from a thermoplastic film-forming polymer. Preferably, the polymer is conformable but not substantially elastomeric. Suitable polymers include, but are not limited to, polyethylene, polypropylene, polyester, polyamides such as nylons, fluoropolymers such as polyvinylidene fluoride (PVDF) or polytetrafluoroethylene (PTFE), and mixtures thereof. The top sheet is preferably a polyolefin film. Preferably, the film has a thickness by weight (ASTM E252-84) of from 10 to 200 micrometers, more preferably from 25 to 100 micrometers.

It is an advantage of the present invention that the top sheet on its wound facing surface may be made hydrophobic so as to reduce adherency of the top sheet to the wound. In alternative embodiments, a medically acceptable adhesive, for example of the kind described above, may be applied to the wound facing surface of the top sheet.

Preferably, the top sheet is formed from a substantially liquid-impermeable sheet material provided with tapered capillaries, each capillary having a base substantially in the plane of the wound facing surface of the top sheet and an apical opening remote from the wound facing surface of the top sheet and preferably in contact with the hydrogel and/or the absorbent layer. The conical capillaries provide rapid one-way wicking of fluid from the front of the top sheet, with minimal wet-back. Top sheets of this type are described in GB-A-1526778.

Preferably, the capillaries are substantially in the form of truncated cones. Preferably, the capillaries have a base opening dimension (the maximum opening dimension in the plane of the top sheet) of from 0.1 mm to 3 mm, and an apical opening dimension (remote from the plane of the top sheet) of from 0.05 to 2 mm. More preferably, the capillaries have a base opening dimension as herein defined of from 0.3 mm to 1 mm, and an apical opening dimension of from 0.1 to 0.5 mm.

Preferably, the capillaries have an average angle of taper (measured from the perpendicular to the plane of the top sheet) of from 10 to 60 degrees. Preferably, the embossed thickness of the top sheet (by ASTM D374-79) is from 0.2 to 2 mm, more preferably from 0.4 to 1 mm.

Top sheets of this type may be manufactured, for example, by embossing or vacuum perforation of a liquid-impermeable thermoplastic film. Preferably, the density of the capillaries is from 10 to 400 per $cm^2$, more preferably from 50 to 200 per $cm^2$. Preferably, the open area of the top sheet is from 5 to 50% of the total area, more preferably from 10 to 25% of the total area.

It has now been found, surprisingly, that the provision of a hydrogel layer adjacent to the back surface of such a top sheet enables a moist wound environment to be maintained for prolonged periods, over a wide range of wound exudation rates. In preferred embodiments, the hydrogel layer is intermediate the top sheet and the optional absorbent layer, and preferably it contacts the back surface of the top sheet, and may be coated or bonded thereto. In use, the top sheet continues to wick away wound fluid to prevent excessive moisture in the wound. When the rate of wound exudate production falls, the hydrogel absorbs moisture vapor from the absorbent layer and preserves a moist wound surface. The hydrogel does not give rise to substantially increased wetback through the top sheet. Loss of hydrogel through the apertures of the top sheet is minimal, and the hydrogel does not interfere with the absorbent layer.

The top sheet provides a physical separation between the hydrogel layer and the wound surface, while enabling the humectant and moisture storage properties of the hydrogel to maintain a desired moisture level at the wound surface.

The term "hydrogel layer" refers to thin, two-dimensional layer, preferably consisting essentially of the hydrogel composition. Preferably it is substantially unitary layer, and preferably it has substantially constant thickness. The layer may be patterned or apertured. Preferably, the hydrogel layer is coextensive with the top sheet. The term "hydrogel layer" does not refer to conventional fibrous absorbent pads having particles of hydrogels, in particular superabsorbents, dispersed therein. The advantages of the invention can be achieved with a thin hydrogel layer, which minimises the cost of the dressing. Preferably, the hydrogel layer has a dry basis weight of from 1 to 2000 $g/m^2$, preferably from 5 to 1000 $g/m^2$, more preferably from 10 to 500 $g/m^2$, still more preferably from 10 to 200 $g/m^2$, still more preferably from 10 to 100 $g/m^2$, and most preferably from 10 to 50 $g/m^2$.

The term "hydrogel" refers generally to materials that interact with the wound fluid under physiological conditions to maintain an elevated moisture level at the wound surface. Preferably, the hydrogel layer forms a gel with water under physiological conditions of temperature and pH. Such hydrogel layers can be formed by the inclusion of medically acceptable macromolecular materials that preferably have the ability to swell and absorb fluid while maintaining a strong integral structure. The hydrogel material is substantially insoluble in water under physiological conditions, whereby the hydrogel is not washed away by the wound fluid. The hydrogel may be a biopolymer, and/or it may be bioabsorbable. That is to say, it may undergo gradual resorption in vivo.

Exemplary insoluble gels include certain cross-linked polyacrylate gels, calcium alginate gels, cross-linked hyaluronate gels, wherein the hydrogel layer comprises a hydrogel material selected from gels formed from vinyl alcohols, vinyl esters, vinyl ethers and carboxy vinyl monomers, meth (acrylic) acid, acrylamide, N-vinyl pyrrolidone, acylamidopropane sulphonic acid, PLURONIC (Registered Trade Mark) (block polyethylene glycol, block polypropylene glycol) polystyrene-, maleic acid, NN-dimethylacrylamide diacetone acrylamide, acryloyl morpholine, and mixtures thereof. Preferably, the gel adheres strongly to the surface of the top sheet material or of the optional absorbent layer or the backing sheet to resist washing off by wound fluid. In certain embodiments the gel may be directly coated or chemically bonded to the back surface of the top sheet.

Preferably, the hydrogel layer comprises a hydrogel material selected from polyurethane gels, biopolymer gels, carboxymethyl cellulose gels, hydroxyethyl cellulose gels, hydroxy propyl methyl cellulose, modified acrylamide and mixtures thereof. Suitable biopolymer gels include alginates, pectins, galactomannans, chitosan, gelatin, hyaluronates and mixtures thereof. Some of these biopolymer materials also promote wound healing.

Preferably, the gels are cross-linked, and the cross-linking may be either covalent or ionic.

Preferably, the hydrogel material further comprises from 5 to 50% by weight on a dry weight basis of one or more humectants such as glycerol.

Preferably, the hydrogel layer comprises a hydrogel material of the kind described in U.S. Pat. No. 6,447,798, the entire contents of which is incorporated herein by reference.

Alternatively or additionally to the gel-forming macromolecules, the hydrogel layer may comprise one or more emollients. Emollients are used to smooth the surface of skin and to increase the degree of hydration. They act either by occluding water loss from the outer layer of the skin, or by improving water binding to the skin. Emollients are particularly useful in the treatment of atopic eczemas and ichthyoses. Preferred emollients include White Soft Paraffin, Yellow Soft Paraffin, Liquid paraffin, Urea Creams, Lanolin, Sodium Pyrrolidone Carboxylate (PCA Na), Evening primrose extract (gamma linolenic acid), Soya Oil, Tea Tree Oil, Coconut Oil, Almond Oil, Camomile Extract, Cod Liver Oil, Peanut Oil, Emu Oil, Aloe Vera, Sunflower oil, Avocado Oil, Jojoba Oil, Cocoamide, and mixtures thereof.

The hydrogel layer may additionally comprise one or more active therapeutic or antimicrobial agents. Suitable therapeutic agents include growth factors, analgesics, local anaesthetics and steroids. Suitable antimicrobial agents include antiseptics such as silver compounds (e.g. silver sulfadiazine) and chlorhexidine, and antibiotics. The therapeutic or antimicrobial agents are usually added in an amount of from 0.01% to 5% by weight, based on the dry weight of the hydrogel layer.

The hydrogel layer may be continuous or discontinuous. Continuous hydrogel layers extend over and cover the apertures in the back of the top sheet. Such continuous layers provide the advantage of temporarily blocking (gel blocking) the passage of wound fluid into the absorbent layer and/or through the backing sheet until the hydrogel is saturated. This helps to prevent drying out of wounds having low rates of exudate production.

In other embodiments, the hydrogel layer is apertured. In some preferred embodiments it is apertured in register with the capillaries in the top sheet so as not to obstruct passage of fluid through the capillaries even when the hydrogel is fully swelled. In other words, there is preferably substantially no hydrogel initially present in or covering the capillaries of the top sheet. The hydrogel layer may be applied by spraying or, preferably, by a printing or transfer process. The apertures may be formed in the hydrogel layer for example by drilling with a hollow needle as described in U.S. Pat. No. 5,076,265, the entire content of which is hereby incorporated by reference. In other embodiments, the apertures may be formed by casting the top sheet in a mold having an array of projections corresponding to the apertures, followed by peeling the hydrogel layer from the mold and applying it in register to the top sheet.

Preferably, the multilayer wound dressing according to the invention further comprises one or more protective cover sheets over the top sheet and any exposed adhesive. For example, these may comprise one or more release-coated paper cover sheets. Preferably, the dressing is sterile and packaged in a microorganism-impermeable container.

The present invention further provides the use of a multilayer wound dressing according to the present invention for the preparation of a dressing for application to a wound.

In a further aspect, the present invention provides a method of treatment of a wound comprising the step of applying a dressing in accordance with the present invention to the surface of the wound with the top sheet contacting the wound.

An embodiment of the present invention will now be described further, by way of example, with reference to the accompanying drawings, in which.

Figure 1:
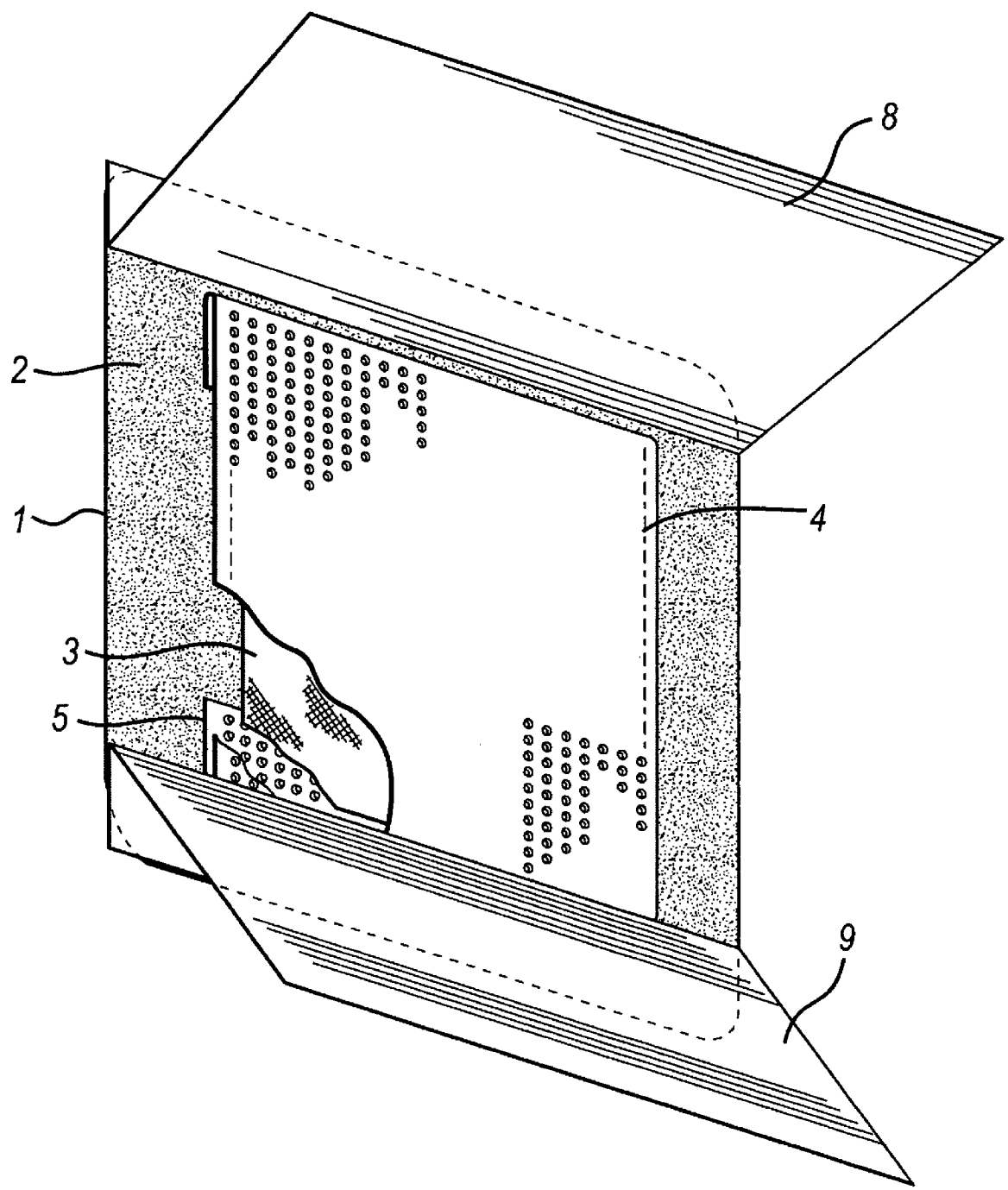
FIG. 1 shows a perspective view of the lower (wound contacting) surface of a wound dressing according to the invention.

Referring to FIG. 1, the wound dressing is an island-type self-adhesive wound dressing comprising a backing layer 1 of microporous liquid-impermeable polyurethane foam, such as ESTANE 5714F (Registered Trade Mark). The backing layer is permeable to water vapor, but impermeable to wound exudate and microorganisms.

The backing layer 1 is coated with a substantially continuous layer 2 of pressure-sensitive polyurethane adhesive.

The absorbent layer 3 is a layer of hydrophilic polyurethane foam prepared as described in EP-A-0541391 and having a basis weight of about 350 g/m$^2$ and a thickness of about 1.5 mm.

The top sheet 4 extends over the absorbent layer 3 and is wrapped partially around the absorbent layer 3 and the edges 5 of the top sheet are adhered to the backing layer 1 behind the absorbent layer 3 by the adhesive 2. This can be seen more clearly in FIG. 2. The top sheet is a polyethylene film that has been perforated with about 90 perforations per cm$^2$, each perforation having a substantially conical shape as hereinbefore described, a maximum hole diameter of about 0.5 mm, an open area of 16% of the total area of the front face a thickness by weight of about 43 micrometers and an embossed thickness of about 0.5 mm. Such top sheets are available from Tredegar Film Products, Richmond, Va. under the Registered Trade Mark VISPORE.

Figure 2:
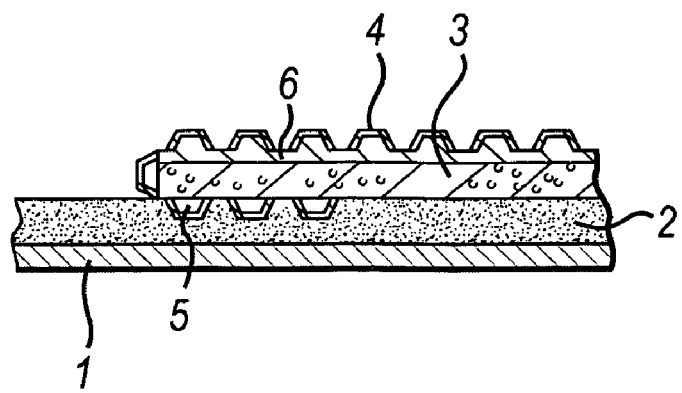
FIG. 2 shows a partial transverse cross section (not to scale) through the island region of the dressing of FIG. 1.
Figure 3:
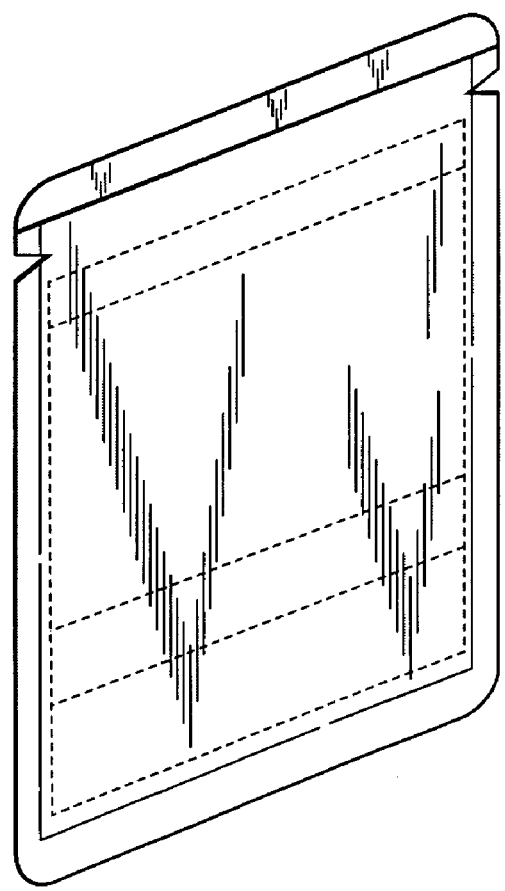
FIG. 3 shows a perspective view of the wound dressing, represented by dashed lines, packaged in a microorganism-impermeable pouch.

Referring to FIG. 2, the top sheet 4 presents a smooth, perforated top surface to the wound The back surface of the top sheet 4 is coated with a layer of hydrogel 6. The hydrogel 6 has a dry basis weight of 30 g/m$^2$ and consists of bovine gelatin cross-linked with glutaraldehyde or formaldehyde.

The wound facing surface of the dressing shown in FIG. 1 is protected by two silicone-coated release papers 8,9, packed in a microorganism-impermeable pouch, and sterilised using gamma radiation.

In use, the dressing is removed from the package, the release papers are removed, and the dressing is adhered to the skin around the wound with the top sheet in contact with the wound to provide a sterile and absorbent dressing. The hydrogel and top sheet interact to provide a moist but not wet wound environment for a wide range of wounds over an extended period.

The above embodiment has been described by way of example only. Many other embodiments falling within the scope of the accompanying claims will be apparent to the skilled reader.

The invention claimed is:

1. A wound dressing comprising: a liquid-permeable top sheet having a wound facing surface and a back surface, said top sheet having greater permeability to the flow of liquid away from the wound facing surface than to the flow of liquid towards the wound facing surface, thereby blocking or restricting passage of liquid from the back surface to the wound facing surface; a hydrogel layer adjacent to and bonded to the back surface of the top sheet; and an absorbent layer adjacent to the hydrogel layer, on the opposite side of the hydrogel from the back surface of the top sheet; wherein the top sheet is formed from a liquid-impermeable sheet material provided with tapered capillaries, each capillary having a base substantially in the wound facing surface of the top sheet and an apical opening remote from the wound facing surface of the top sheet; wherein the capillaries are substantially in the form of truncated cones; and wherein the hydrogel layer is apertured in register with apertures in the top sheet, wherein said wound dressing maintains a suitably moist wound environment.

2. A wound dressing according to claim 1, wherein the absorbent layer comprises a layer of hydrophilic foam, a superabsorbent, or a combination thereof.

3. A wound dressing according to claim 1, wherein the absorbent layer further comprises a medicament.

4. A wound dressing according to claim 1, wherein the dressing further comprises a substantially liquid-impermeable backing layer over the absorbent layer.

5. A wound dressing according to claim 4, further comprising a layer of adhesive on the surface of the backing layer facing the top sheet.

6. A wound dressing according to claim 5, wherein the backing layer extends beyond at least one edge of the absorbent layer to provide an adhesive-coated margin adjacent to said edge for adhering the dressing to a surface.

7. A wound dressing according to claim 1, wherein the top sheet comprises a porous, substantially hydrophobic, non-woven fabric.

8. A wound dressing according to claim 1, wherein the capillaries have a base opening dimension from 0.15 mm to 6 mm, and an apical opening dimension of from 0.1 to 2.5 mm.

9. A wound dressing according to claim 8, wherein the capillaries have a base opening dimension of from 0.5 mm to 1.5 mm, and an apical opening dimension of from 0.1 to 0.5 mm.

10. A wound dressing according to claim 1, wherein the capillaries have an average angle of taper of from 10 to 60 degrees.

11. A wound dressing according to claim 1, wherein the hydrogel layer has a dry basis weight from 10 to 200 $g/m^2$.

12. A wound dressing according to claim 1, wherein the hydrogel layer comprises a hydrogel material selected from polyurethane gels, biopolymer gels, carboxymethyl cellulose gels, hydroxyethyl cellulose gels, hydroxypropyl methyl cellulose, modified acrylamides and mixtures thereof.

13. A wound dressing according to claim 1, wherein the hydrogel layer comprises a hydrogel material selected from gels formed from vinyl alcohols, vinyl esters, vinyl ethers and carboxy vinyl monomers, meth(acrylic) acid, acrylamide, N-vinyl pyrrolidone, acylamidopropane sulphonic acid, plutonic (block polyethylene glycol, block polypropylene glycol)polystyrene maleic acid, NN-dimethylacrylamide, diacetone acrylamide or acryloyl morpholine.

14. A wound dressing according to claim 1, wherein the hydrogel layer comprises an emollient.

15. A wound dressing according to claim 14, wherein the emollient is selected from the group consisting of white soft paraffin, yellow soft paraffin, liquid paraffin, urea creams, lanolin, sodium pyrrolidone carboxylate, evening primrose extract (gamma linolenic acid), soya oil, tea tree oil, coconut oil, almond oil, camomile extract, cod liver oil, peanut oil, emu oil, aloe vera, sunflower oil, avocado oil, jojoba oil, cocoamide, and mixtures thereof.

16. A wound dressing according to claim 1, wherein the hydrogel layer comprises an active therapeutic agent or an antimicrobial agent.

17. A wound dressing according to claim 16, wherein the hydrogel layer comprises a silver compound.

18. A wound dressing according to claim 1, further comprising one or more protective cover sheets over the wound facing surface of the top sheet.

19. A wound dressing according to claim 1, wherein the dressing is sterile and packaged in a microorganism-impermeable container.

20. A method of treating a wound comprising the step of applying a wound dressing comprising a liquid-permeable top sheet having a wound facing surface and a back surface, said to sheet having greater permeability to the flow of liquid away from the wound facing surface than to the flow of liquid towards the wound facing surface, thereby blocking or restricting passage of liquid from the back surface to the wound facing surface; a hydrogel layer adjacent to and bonded to the back surface of the top sheet; and all absorbent layer adjacent to the hydrogel layer, on the opposite side of the hydrogel from the back surface of the top sheet; wherein the top sheet is formed from a liquid-impermeable sheet material provided with tapered capillaries, each capillary having a base substantially in the wound facing surface of the top sheet and an apical opening remote from the wound facing surface of the top sheet; wherein the capillaries are substantially in the form of truncated cones; and wherein the hydrogel layer is apertured in register with apertures in the to sheet, wherein said wound dressing maintains a suitably moist wound environment, to the wound with said top sheet contacting said wound.

21. A wound dressing according to claim 1, wherein the hydrogel layer has a dry basis weight of form 10 to 100 $g/m^2$.

22. A wound dressing according to claim 1, wherein the hydrogel layer is bonded to the back surface of the top sheet.

* * * * *